(12) United States Patent
Wu et al.

(10) Patent No.: US 11,052,058 B2
(45) Date of Patent: Jul. 6, 2021

(54) USE OF POULTRY CRUDE PROTEIN EXTRACT FOR PREPARING ANTI-FATIGUE COMPOSITION

(71) Applicant: Yuan Jin Chuang Enterprise Co., Ltd, New Taipei (TW)

(72) Inventors: Hung-Yuan Wu, Yunlin County (TW); Meng-Hui Lin, Yunlin County (TW)

(73) Assignee: Yuan Jin Chuang Enterprise Co., Ltd, New Taipei (TW)

( * ) Notice: Subject to any disclaimer, the term of this patent is extended or adjusted under 35 U.S.C. 154(b) by 58 days.

(21) Appl. No.: 16/253,190

(22) Filed: Jan. 21, 2019

(65) Prior Publication Data
US 2019/0247346 A1 Aug. 15, 2019

(30) Foreign Application Priority Data
Feb. 13, 2018 (TW) .................. 107105385

(51) Int. Cl.
| | | |
|---|---|---|
| *A61K 31/198* | (2006.01) | |
| *A23J 1/02* | (2006.01) | |
| *A61K 31/4172* | (2006.01) | |
| *A61P 39/06* | (2006.01) | |
| *A23L 33/175* | (2016.01) | |

(52) U.S. Cl.
CPC ............ *A61K 31/198* (2013.01); *A23J 1/02* (2013.01); *A23L 33/175* (2016.08); *A61K 31/4172* (2013.01); *A61P 39/06* (2018.01); *A23V 2002/00* (2013.01)

(58) Field of Classification Search
CPC ..... A61K 31/198; A61K 31/4172; A23J 1/02; A61P 39/06; A23L 33/175; A23L 33/17; A23V 2002/00
See application file for complete search history.

(56) References Cited

U.S. PATENT DOCUMENTS

2009/0104278 A1    4/2009   Murakami et al.

FOREIGN PATENT DOCUMENTS

| | | |
|---|---|---|
| CN | 107397761 | * 11/2017 |
| CN | 108420854 | 8/2018 |
| JP | 3617102 | * 11/2004 |
| TW | I256882 | 6/2006 |
| TW | I586357 | 6/2017 |

\* cited by examiner

*Primary Examiner* — Sahar Javanmard
(74) *Attorney, Agent, or Firm* — JCIP Global Inc.

(57) ABSTRACT

A use of a poultry crude protein extract for preparing an anti-fatigue composition is provided. The poultry crude protein extract is obtained by extraction of poultry meat at high temperature and high pressure and the removal of fat by oil and water separation, and the poultry crude protein extract includes at least branched-chain amino acid (BCAA), histidine, threonine, lysine, and phenylalanine, wherein anti-fatigue entails increasing muscle glycogen concentration, helping to increase exercise tolerance, helping to increase blood urea nitrogen metabolism, and helping to inhibit lactic acid production.

11 Claims, No Drawings

USE OF POULTRY CRUDE PROTEIN EXTRACT FOR PREPARING ANTI-FATIGUE COMPOSITION

CROSS-REFERENCE TO RELATED APPLICATION

This application claims the priority benefit of Taiwan application serial no. 107105385, filed on Feb. 13, 2018. The entirety of the above-mentioned patent application is hereby incorporated by reference herein and made a part of this specification.

BACKGROUND OF THE INVENTION

Field of the Invention

The invention provides a poultry crude protein extract, and more particularly, to a use of a poultry crude protein extract for preparing an anti-fatigue composition.

Description of Related Art

Fatigue means that the body cannot maintain a certain level of operation, and each organ cannot maintain a fixed working ability; that is, the working muscle of the body is unable to maintain strength due to excessive activity, resulting in decreased activity ability.

The cause of fatigue is known to be due to energy depletion, accumulation of metabolites, and damage to free radicals. Glucose in the blood is metabolized during prolonged exercise to provide muscle tissue energy. When the blood sugar level is insufficient to provide sufficient energy, the glycogen is decomposed to form glucose and released into the blood. Studies have shown that glycogen content in muscle may be used as a related index of long-term muscle exercise. When a large amount of energy is consumed, anaerobic glucose metabolism in the body is promoted to increase a large amount of ATP in a short time, and at the same time a large amount of lactic acid accumulation is produced, and therefore the hydrogen ion concentration is increased and the pH value is lowered, which leads to the release of calcium ions and reduction in the contraction ability of the muscle fibers, thereby accelerating the occurrence of fatigue. Studies have shown that it takes 5 to 10 minutes for lactic acid in muscle and blood to reach equilibrium, and lactic acid may be removed by conversion to glucose or glycogen. Therefore, accelerating the metabolism of lactic acid is an important index for recovering from fatigue.

Blood urea nitrogen is the final product of protein and amino acid metabolism in the human body, and the decomposition rate and metabolic rate of protein affect the blood urea nitrogen concentration. Exercise causes intense decomposition of proteins and amino acids, decreased function of the kidneys, and dehydration such that a decrease in plasma volume occurs, which leads to a decrease in blood flow to the kidneys and a large decomposition of proteins and amino acids, which all cause an increase in blood urea nitrogen concentration.

Free radicals are elements such as atoms, molecules, and ions. Their peripheral orbitals contain structures that are separate pairs of electrons, which easily combine electrons from other surrounding cellular molecules to trigger a series of reactions that cause oxidative stress. In the case of long-term or intense exercise, free radicals are generated in large quantities, causing a large amount of oxidative stress. If the antioxidant defense system is not enough to compete, the body's cellular tissue is damaged, resulting in physiological function disorders.

When fatigue occurs, problems such as slow response and inability to perform precise operations occur, which increase the errors in machine operation and the occurrence of danger. Therefore, how to supplement which substances or ingredients from daily life to prevent fatigue has always been a major issue in the food, nutrition, health care, and medical fields.

SUMMARY OF THE INVENTION

Accordingly, the invention provides a use of a poultry crude protein extract for preparing an anti-fatigue composition, wherein the poultry crude protein extract is obtained by an extraction of a poultry meat at a high temperature of 85° C. to 105° C. and a high pressure for 9 hours to 11 hours and a removal of a fat by an oil and water separation, and the poultry crude protein extract includes at least branched-chain amino acid (BCAA), histidine, threonine, lysine, and phenylalanine.

The invention further provides a use of a poultry crude protein extract for preparing a composition for increasing a muscle glycogen concentration, wherein the poultry crude protein extract is obtained by an extraction of a poultry meat at a high temperature and a high pressure and a removal of a fat by an oil and water separation, and the poultry crude protein extract includes at least branched-chain amino acid (BCAA), histidine, threonine, lysine, and phenylalanine.

The invention further provides a use of a poultry crude protein extract for preparing a composition for increasing an exercise tolerance, wherein the poultry crude protein extract is obtained by an extraction of a poultry meat at a high temperature and a high pressure and a removal of a fat by an oil and water separation, and the poultry crude protein extract includes at least branched-chain amino acid (BCAA), histidine, threonine, lysine, and phenylalanine.

The invention further provides a use of a poultry crude protein extract for preparing a composition for increasing a blood urea nitrogen metabolism, wherein the poultry crude protein extract is obtained by an extraction of a poultry meat at a high temperature and a high pressure and a removal of a fat by an oil and water separation, and the poultry crude protein extract includes at least branched-chain amino acid (BCAA), histidine, threonine, lysine, and phenylalanine.

The invention further provides a use of a poultry crude protein extract for preparing a composition for inhibiting a lactic acid production, wherein the poultry crude protein extract is obtained by an extraction of a poultry meat at a high temperature and a high pressure and a removal of a fat by an oil and water separation, and the poultry crude protein extract includes at least branched-chain amino acid (BCAA), histidine, threonine, lysine, and phenylalanine.

In an embodiment of the invention, the poultry crude protein extract further includes tyrosine and methionine.

In an embodiment of the invention, an effective dose of the poultry crude protein extract is at least 20 mL per day.

In an embodiment of the invention, a source of the poultry meat is chicken, duck, goose, or pigeon.

The poultry crude protein extract of the invention does not affect animal weight, food intake, liver weight, and kidney weight, and has no adverse effects on physiological metabolism. The values of liver damage (AST, ALT) and muscle damage (CPK, creatinine) indices show that feeding of the poultry crude protein extract of the invention had no adverse effects on the safety of rats. The liver and muscle oxidative damage indices show that the feeding of the poultry crude protein extract of the invention increased the activity of antioxidant enzymes and formed a protective effect. Swimming exhaustion test results show that, the swimming time increased significantly when the poultry crude protein extract of the invention was fed; the evaluation results of metabolic stress biochemical indices show that in terms of lactic acid production, lactic acid production is lower when the poultry crude protein extract of the invention was fed; in terms of liver and muscle glycogen concentrations, the muscle glycogen concentration shows a significant increase when the poultry crude protein extract of the invention was fed. Therefore, the poultry crude protein extract of the invention has the effects of increasing muscle glycogen concentration, helping to increase exercise tolerance, helping to increase blood urea nitrogen metabolism, and helping to inhibit lactic acid production.

The embodiments of the invention are further described below in conjunction with the drawings. The following embodiments are used to illustrate the invention, and are not intended to limit the scope of the invention, and any person skilled in the art, without departing from the spirit and scope of the invention, may perform slight alterations and modifications, and therefore the scope of the invention is defined by the claims at the end.

DESCRIPTION OF THE EMBODIMENTS

When fatigue occurs, the reaction is slow and precision operation cannot be performed, which increases operational errors and dangers. When the human body undergoes hypoxia or intense exercise, the blood glucose concentration is increased by the conversion of glycogen into glucose. Anti-fatigue effects may be achieved by providing sufficient energy to muscle tissue through glycolysis, reducing the production of lactic acid in the human body after anaerobic exercise, removing lactic acid in time, or increasing the antioxidants in the body.

The invention provides a use of a poultry crude protein extract for preparing an anti-fatigue composition. In the invention, to evaluate the effect of the poultry crude protein extract on fatigue resistance, the specifications of "Anti-fatigue function evaluation method for healthy foods" issued by the Health and Welfare Department were referenced, and an experiment was carried out with 9-week-old Sprague-Dawley (SD)-strain male rats, with 8 rats in each group that were respectively the control group, Low-dose group, medium-dose group, and high-dose group. After 8 weeks of feeding the poultry crude protein extract of the invention, an evaluation of physical fitness challenge and fatigue elimination indices was performed.

Definitions

The poultry crude protein extract described by the specification includes crude protein extracts of poultry such as chickens, ducks, geese, and pigeons.

The "anti-fatigue" described in the specification refers to an increase in muscle glycogen concentration, an increase in exercise tolerance, an increase in blood urea nitrogen metabolism, and an inhibition of lactic acid production.

As the values used in the specification are approximate, all experimental data are expressed in the range of 20%, preferably in the range of 10%, and most preferably in the range of 5%.

Statistical Analysis

According to the general biostatistical method analysis, the SPSS statistical software was integrated and expressed as mean±standard deviation (S.D.) The test data compared the recovery evaluation of the fatigue challenge after the intervention of the test substance using the Duncan's Multiple Range Test of one-way ANOVA in the statistical software. The statistical results are expressed in English letters. The same letter indicates that there is no statistical difference between the groups ($p>0.05$), and different letters indicate statistical difference between the groups ($p<0.05$). After the intervention of the test substance and after the appropriate fatigue challenge, the recovery evaluation index has at least two types of indices to achieve statistically significant improvement ($p<0.05$), and it may be determined that the test substance should have anti-fatigue function.

Example 1 Method for Preparing Poultry Crude Protein Extract of the Invention

In the invention, 15-week old white Muscovy duck test No. 1 was used, which after being slaughtered, was placed in an environment at a temperature of $-2°$ C. to $7°$ C. for acceptance and raw material treatment. Duck meat that was normal in color without exudate on the surface and odor that was elastic was placed in a pressure cooker, and then concentrated and extracted at a set temperature of $95°$ C. under reduced pressure for 10 hours, and then was subjected to oil and water separation and hot filling at $85°$ C., and lastly sterilized at $121°$ C. for 15 minutes to obtain the poultry crude protein extract of the invention.

Example 2 Ingredient Analysis of Poultry Crude Protein Extract of the Invention

In the invention, an ingredient analysis was further performed on the duck crude protein extract prepared in Example 1 and the chicken crude protein extract prepared by the same method, and the results are shown in Table 1 and Table 2, which include amino acid and protein, and have higher content of amino acids such as lysine, histidine, lysine, phenylalanine, isoleucine, leucine, and lysine, especially leucine, which is an amino acid necessary for the human body.

Since these amino acids cannot be synthesized by the liver, they must be obtained by additional intake; they may reduce the feeling of fatigue, and for those who perform physical exercise, leucine is a precursor of α-ketoisocaproate (KIC) and β-hydroxy-β-methylbutyrate (HMB), which may improve exercise capacity and accelerate the recovery of muscle fatigue. Furthermore, it was further confirmed in the nutrient analysis that the poultry crude protein extract of the invention contained no trans-fat and had a very low content of saturated fat, which is beneficial to human health.

TABLE 1

Analysis of amino acids in duck crude protein extract and chicken crude protein extract (mg/100 g)

| Amino acid | Histidine His | Threonine Thr | Tyrosine Tyr | Valine Val | Methionine Met | Phenylalanine Phe | Isoleucine Ile | Leucine Leu | Lysine Lys |
|---|---|---|---|---|---|---|---|---|---|
| Duck crude protein extract | 75.4 | 111.7 | 37.2 | 115.0 | 54.8 | 101.7 | 79.7 | 193.0 | 232.6 |
| Chicken crude protein extract | 91.3 | 105.1 | 22.7 | 119.2 | 51.9 | 132.3 | 83.6 | 166.2 | 219.2 |

TABLE 2

Analysis of nutrients of duck histone extract and chicken histone extract

| Nutrition label | Water content (%) | Ash content (%) | Fat (%) | Protein (%) | Saturated fat (%) | Trans fat (%) | Carbohydrate (%) | Sugar (%) | Sodium (mg/100 g) | Total calories (K cal/100 g) |
|---|---|---|---|---|---|---|---|---|---|---|
| Duck crude protein extract | 92.6 | 0.7 | 0.2 | 7.2 | 0.08 | 0.00 | 0 | 0.0 | 98.6 | 30.6 |
| Chicken crude protein extract | 92.7 | 0.8 | 0.1 | 6.7 | 0.06 | 0.00 | 0 | 0.0 | 89.0 | 27.7 |

Example 3 Anti-Fatigue Evaluation of Poultry Crude Protein Extract of the Invention In the invention, to evaluate the effects of poultry crude protein extract on anti-fatigue function, the specifications of the "Evaluation Method of Anti-Fatigue Function for Healthy Foods" issued by the of Health and Welfare Department were referenced, and an experiment was performed with 9-week-old SD-strain male rats (purchased from Lesco Biotech Co., Ltd.) There were 8 rats in each group, which were respectively the control group, low-dose group, medium-dose group, and high-dose group. The low-, medium-, and high doses of the poultry crude protein extract of the invention administered were respectively 0.58, 1.17, 2.92 g/kg BW (body weight), and the control group was given reverse osmosis water (oral dose of rats was calculated according to the daily intake of adults, as shown in Table 3).

TABLE 3

Feeding dose of each group of poultry crude protein extract of the invention

| Animal group | Tube feeding substance | Dose$^a$ (g/kg) | Relative human dose$^b$ (g/60 kg) | Number of animals |
|---|---|---|---|---|
| Control group | Reverse osmosis water | — | — | 8 |
| Low-dose group | Poultry crude protein extract | 20.7 | 5.66 | 8 |
| Medium-dose group | Poultry crude protein extract | 41.3 | 11.31 | 8 |

TABLE 3-continued

Feeding dose of each group of poultry crude protein extract of the invention

| Animal group | Tube feeding substance | Dose$^a$ (g/kg) | Relative human dose$^b$ (g/60 kg) | Number of animals |
|---|---|---|---|---|
| High dose-group | Poultry crude protein extract | 103.5 | 28.28 | 8 |

$^a$Dose conversion: The dose of oral administration of rats was based on the daily intake of adults, and then conversion was performed according to the metabolic coefficient (6.2) of the rats relative to the human body and the daily oral dose of the rats was calculated. Taking 1 g per person per day as an example, the rat dose was 0.103 g/kg (1 g/60 kg × 6.2 = 0.103 g/kg).
$^b$The poultry crude protein extract of the invention was fed for 8 weeks. The specification was 65 mL/bottle and the freeze-dry ratio was 8.7%, and therefore the freeze-dried weight was 5.66 g/bottle.

After 8 weeks of feeding the poultry crude protein extract of the invention, an evaluation of physical fitness challenge and fatigue elimination indices was performed. The physical challenge was a swimming exhaustion test, and a fatigue evaluation was performed after the test. The evaluation of physiological stress recovery included metabolic stress indices: increased lactate rate, decreased lactate rate, and blood urea nitrogen (BUN) content. Muscle damage index: creatinine, creatinine phosphokinase (CPK), and myoglobin. Liver damage index: aspartate aminotransferase (AST) and alanine aminotransferase (ALT) activity. Oxidative damage index: thiobarbituric acid reactive substances (TBARS), catalase, superoxide dismutase (SOD) and glutathione peroxidase (GPx) activity.

Before the start of the test, the rats were quarantined and adapted for one week, making the rats used to and familiar with the new environment. On the first day of the test, the poultry crude protein extract of the invention was administered daily until the 56th day; on the 49th day, swimming training was performed to facilitate the swimming test afterwards; on the 52nd day, a swimming exhaustion test was performed with a load of 3% of the bodyweight; on the 53rd day, after a 90-minute swimming test was performed, the blood urea nitrogen (BUN) value was measured; on the 55th day, after an oil test was performed for 10 minutes, the serum lactate value was measured before swimming, after swimming, and after 20 minutes of rest; on the 56th day, a physiological and biochemical analysis was performed after animal sacrifice and blood collection were performed.

3.1 Determination of Bodyweight and Food Intake

The test animals were measured for bodyweight and food intake once a week before and during the test; and the measurement was performed once a week during the test. The measurement method was to add a quantitative feed on the day of the weight measurement, and the remaining feed amount was calculated one week later. As shown in Tables 4 and 5, the test results show that the average bodyweight and food intake of low-, medium-, and high doses in the first to eighth weeks of the test are not significantly different from those in the control group (p>0.05).

TABLE 4

Changes in average bodyweight of rats in each group during the test period

| Feeding week | Control group | Low-dose group (0.58 g/kg) | Medium-dose group (1.17 g/kg) | High-dose group (2.92 g/kg) |
|---|---|---|---|---|
| | | Weight (g) | | |
| Before test | 349.9 ± 8.0$^a$ | 354.6 ± 9.2$^a$ | 352.6 ± 11.3$^a$ | 353.6 ± 11.0$^a$ |
| First week | 397.9 ± 9.1$^a$ | 402.0 ± 13.7$^a$ | 394.6 ± 10.8$^a$ | 406.0 ± 13.4$^a$ |
| Second week | 432.4 ± 10.6$^a$ | 434.5 ± 18.5$^a$ | 424.3 ± 16.1$^a$ | 440.1 ± 13.8$^a$ |
| Third week | 467.0 ± 9.0$^a$ | 458.3 ± 13.3$^a$ | 453.0 ± 17.2$^a$ | 468.8 ± 17.2$^a$ |
| Fourth week | 491.2 ± 12.4$^a$ | 488.7 ± 22.4$^a$ | 481.0 ± 17.0$^a$ | 495.1 ± 20.3$^a$ |
| Fifth week | 515.1 ± 13.3$^a$ | 516.8 ± 27.0$^a$ | 517.8 ± 27.2$^a$ | 520.4 ± 23.2$^a$ |
| Sixth week | 534.0 ± 19.4$^a$ | 542.3 ± 28.8$^a$ | 538.4 ± 25.0$^a$ | 542.8 ± 23.0$^a$ |
| Seventh week | 562.7 ± 20.0$^a$ | 569.5 ± 25.7$^a$ | 566.3 ± 24.1$^a$ | 567.4 ± 22.5$^a$ |
| Eighth week | 575.6 ± 20.9$^a$ | 580.2 ± 21.9$^a$ | 576.3 ± 18.2$^a$ | 579.4 ± 14.0$^a$ |

All data are expressed as mean±S.D., n=8. The difference between the groups was compared by fmultiple range test of One-Way ANOVA, and the statistical results are represented by English letters. The same letter indicates that there is no statistical difference between the groups (p>0.05), and different letters indicate statistical difference between the groups (p<0.05).

TABLE 5

Changes in average food intake of rats in each group during the test period

| Feeding week | Control group | Low-dose group (0.58 g/kg) | Medium-dose group (1.17 g/kg) | High-dose group (2.92 g/kg) |
|---|---|---|---|---|
| | | Food intake (g/day/rat) | | |
| First week | 27.6 ± 1.7$^a$ | 27.5 ± 1.6$^a$ | 27.2 ± 2.6$^a$ | 27.1 ± 2.0$^a$ |
| Second week | 29.7 ± 0.7$^a$ | 30.7 ± 1.7$^a$ | 29.5 ± 1.2$^a$ | 29.6 ± 2.5$^a$ |
| Third week | 28.1 ± 1.1$^a$ | 28.2 ± 2.0$^a$ | 27.3 ± 1.7$^a$ | 27.7 ± 1.6$^a$ |
| Fourth week | 28.1 ± 1.6$^a$ | 27.7 ± 2.1$^a$ | 27.5 ± 1.3$^a$ | 27.1 ± 1.8$^a$ |
| Fifth week | 27.7 ± 0.9$^a$ | 27.2 ± 1.6$^a$ | 27.1 ± 1.1$^a$ | 26.9 ± 2.0$^a$ |
| Sixth week | 28.0 ± 1.5$^a$ | 27.3 ± 1.6$^a$ | 27.3 ± 1.2$^a$ | 27.0 ± 2.1$^a$ |
| Seventh week | 27.9 ± 2.0$^a$ | 27.5 ± 1.9$^a$ | 27.5 ± 0.7$^a$ | 26.9 ± 2.1$^a$ |
| Eighth week | 26.6 ± 1.0$^a$ | 27.4 ± 1.9$^a$ | 27.7 ± 0.9$^a$ | 26.5 ± 1.9$^a$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

3.2 Determination of Liver and Kidney Weight

At the end of rats sacrifice in the test, the livers and kidneys of the rats in each group were weighed and statistically analyzed. The results of the test period are shown in Table 6. There is no significant difference in the weight of liver and kidney between the rats of each group and the control group (p>0.05).

TABLE 6

Average weight of liver and kidney of rats in each group

| Item | Control group | Low-dose group (0.58 g/kg) | Medium-dose group (1.17 g/kg) | High-dose group (2.92 g/kg) |
|---|---|---|---|---|
| Liver weight (g) | 20.6 ± 3.6$^a$ | 21.9 ± 2.5$^a$ | 21.0 ± 1.8$^a$ | 21.6 ± 2.5$^a$ |
| Kidney weight (g) | 3.9 ± 0.4$^a$ | 4.1 ± 0.2$^a$ | 3.8 ± 0.4$^a$ | 4.0 ± 0.5$^a$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

3.3 Swimming Exhaustion Test

One week before the experiment, after 30 minutes of feeding, swimming training was first performed. After fasting for 12 hours before the test, the rats were placed in a plastic bucket with a diameter of 45 cm, a water depth of 50 cm, and a water temperature of 27±1° C. for weight-bearing swimming. The weight-bearing ratio was 3% of the bodyweight, forcing the rats to struggle during the swim until physical exhaustion and sinking, then the time from when the rats were in the water to when their nostrils sank into the water for 10 seconds was used as the swimming time.

The results of swimming exhaustion time of rats in each group are shown in Table 7. After low-, medium-, and high doses of the poultry crude protein extract of the invention were fed, the swimming times of the rats were respectively increased compared to the control group from 442.3 seconds to 598.8 seconds, 571.3 seconds, and 585.6 seconds. It is observed that the swimming time of the animals after being fed the poultry crude protein extract of the invention is increased significantly (p<0.05), but there is no significant difference between the doses (p>0.05).

TABLE 7

Time of swimming exhaustion for rats in each group

| Item | Control group | Low-dose group (0.58 g/kg) | Medium-dose group (1.17 g/kg) | High-dose group (2.92 g/kg) |
|---|---|---|---|---|
| Swimming exhaustion time (sec) | 442.3 ± 70.2$^a$ | 598.8 ± 145.1$^b$ | 571.3 ± 90.0$^b$ | 585.6 ± 116.4$^b$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

3.4 Lactic Acid Biochemical Analysis Measurement

After a 10-minute swimming test, the serum lactate value was measured before swimming, after swimming, and after 20 minutes of rest, and serum was obtained and lactic acid content was measured with a serum biochemical analyzer (7070 Autoanalyzer, Hitachi). Regarding the change of lactic acid content after the swimming exhaustion test, it may be observed from the results of Table 8 that the rate of increase in lactic acid of the low-, medium-, and high-dose groups is significantly reduced compared with the control group, showing a significant difference (p<0.05); however, there is no significant difference in the rate of decrease in lactic acid in each dose group compared with the control group (p>0.05). In addition, there is no significant difference in the rate of increase in lactic acid and the rate of decrease in lactic acid between the doses (p>0.05).

3.5 Blood Urea Nitrogen Biochemical Analysis Measurement

After a 90-minute swimming test, blood urea nitrogen content (BUN) was measured. Serum was obtained and blood urea nitrogen content was measured by a serum biochemical analyzer (7070 Autoanalyzer, Hitachi). The analysis results of blood urea nitrogen content are shown in Table 8. It may be found that after feeding the poultry crude protein extract of the invention, the blood urea nitrogen value of each dose group is significantly lower than that of the control group (p<0.05), but there is no significant difference between the doses (p>0.05).

3.6 Liver and Muscle Tissue Liver Analysis 30 minutes after the current feeding, the animals were sacrificed, the liver and calf gastrocnemius muscles were taken, the glycogen was decomposed into glucose, and the glycogen was measured by a commercially available kit of onion ketone reagent. The analysis results of liver and muscle glycogen concentration are shown in Table 8. The liver glycogen concentration results show that there is no significant difference between the low-, medium-, and high-dose groups and the control group (p>0.05). The results of muscle glycogen concentration show that the low-, medium-, and high-dose groups show a significant increase compared with the control group (p<0.05), but there is no significant difference between the doses (p>0.05).

TABLE 8

Blood urea nitrogen, rate of increase in lactic acid and decrease in lactic acid, liver and muscle glycogen analysis results of rats in each group

| Item | Control group | Low-dose group (0.58 g/kg) | Medium-dose group (1.17 g/kg) | High-dose group (2.92 g/kg) |
|---|---|---|---|---|
| BUN (mg/dL) | 24.0 ± 7.6$^b$ | 18.7 ± 1.4$^a$ | 19.7 ± 1.2$^a$ | 19.5 ± 1.4$^a$ |
| Increased lactate rate (%) | 116.2 ± 51.9$^b$ | 67.1 ± 40.9$^a$ | 66.1 ± 33.6$^a$ | 57.8 ± 27.9$^a$ |
| Decreased lactate rate (%) | 40.0 ± 13.8$^a$ | 54.8 ± 13.7$^a$ | 53.8 ± 15.4$^a$ | 53.6 ± 10.6$^a$ |
| Glycogen (mg/g liver tissue) | 20.4 ± 6.4$^a$ | 21.6 ± 5.1$^a$ | 19.5 ± 2.8$^a$ | 16.6 ± 4.8$^a$ |
| Glycogen (mg/g muscle tissue) | 0.82 ± 0.30$^a$ | 1.72 ± 0.58$^b$ | 1.88 ± 0.42$^b$ | 1.64 ± 0.60$^b$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

3.7 Factor Analysis of Oxidative Damage Index in Liver and Muscle Tissue

In the invention, the degree of oxidative damage in liver and muscle tissue was measured via thiobarbituric acid reactive substances (TBARS), catalase, superoxide dismutase (SOD), and glutathione peroxidase (GPx) activity.

The thiobarbituric acid (TBA) reactive substances were based on the lipid peroxidation test of Tarladgis et al., in which 1,1,3,3-tetramethoxy-propane (TMP) was used as the standard, and TMP was diluted to 1 mM with double distilled water first, and then the concentration thereof was respectively diluted to 0, 20, 40, 60, 80, and 100 μM with 1 N $H_2SO_4$ solution, and 100 μL of each was analyzed. The analysis method was the same as the sample. 100 μL of tissue extract was added to 600 μL of 5% trichloroacetic acid and 200 μL of 60 mmol/L TBA, and after reacting at 80° C. for 90 minutes, the tissue extract was cooled to room temperature, and after centrifugation (12,000×g, 15 min, 4° C.), the supernatant was removed for analysis of malondialdehyde (MDA) concentration. After MDA and thiobarbituric acid solution were heated for a period of time in an acidic environment, a pink substance was produced, and the absorbance at a wavelength of 540 nm was measured to estimate the degree of "lipid peroxidation" of the sample. Thiobarbituric acid is a product from the analysis of the lipid peroxidation effect and is generally expressed in terms of MDA production, and the measurement unit is expressed in μM/g protein.

The principle of catalase measurement is that catalase may catalyze the decomposition of $H_2O_2$ into $H_2O$ and $O_2$ and decrease the absorbance of $H_2O_2$ with time. Since the reaction amount is proportional to the decrease rate of absorption value, the rate of decomposition of $H_2O_2$ is used to quantify catalase activity. The activity of catalase is expressed in U/g protein. $H_2O_2$ was diluted with phosphate buffered saline (PBS; 0.05 M $NaH_2PO_4$, and $Na_2HPO_4$), and a test was performed with an absorbance thereof between about 1.2 and 1.3 to prepare catalase (20, 40, 60, 70, 80, 90, 100 unti/mL/protein), and after 900 μL $H_2O_2$ dilution was uniformly mixed with 100 μL of the sample, the amount of change in the absorbance at a wavelength of 230 nm in 3 minutes was measured by a spectrophotometer for quantitative analysis.

The activity of superoxide dismutase (SOD) was analyzed according to the SOD activity test reagent Ransod (RANDOX Lab Ltd., UK). The SOD activity is defined as the inhibition of 2-(4-iodo-phenyl)-3-(4-nitro-phenyl)-5-phenyltetrazolium chloride, wherein the amount of enzyme required to reduce the reaction rate by 50% is one unit (U), and the measurement unit is expressed as U/mg protein.

The glutathione peroxidase (GPx) measurement was based on GPx activity test reagent Ransel (RANDOX Lab Ltd., UK). GPx activity is defined as one unit (U) of the amount of enzyme required to oxidize 1 mole of NADPH per minute, and the GPx activity of the tissue is expressed as U/mg protein.

The oxidative damage index of liver of rats in each group is as shown in Table 9. The GPx activity of the low-, medium-, and high-dose groups is significantly higher than that of the control group (p<0.05); the SOD activity of the low-dose group is not significantly different from that of the control group (p>0.05), and the SOD activity is significantly increased in the middle- and high-dose groups compared with the control group (p<0.05); the catalase activity of the low-, medium-, and high-dose groups is higher than that of the control group (p<0.05), and there is no significant difference between the doses (p>0.05); the content of thiobarbituric acid reactive substance (TBARS) of each dose group is significantly lower than that of the control group (p<0.05), and there is no difference between groups (p>0.05).

TABLE 9

Analysis results of oxidative damage index of liver tissue of rats in each group

| Item | Control group | Low-dose group (0.58 g/kg) | Medium-dose group (1.17 g/kg) | High-dose group (2.92 g/kg) |
|---|---|---|---|---|
| GPx (U/g protein) | 452.8 ± 47.4$^a$ | 533.2 ± 71.5$^b$ | 552.0 ± 63.5$^{bc}$ | 603.5 ± 74.7$^c$ |
| SOD (U/mg protein) | 22.4 ± 7.3$^a$ | 20.4 ± 5.9$^a$ | 30.1 ± 5.1$^b$ | 30.5 ± 9.3$^b$ |
| Catalase (U/g protein) | 1,598.2 ± 324.3$^a$ | 2,116.3 ± 537.9$^b$ | 2,289.2 ± 671.2$^b$ | 3,129 ± 381.0$^c$ |

TABLE 9-continued

Analysis results of oxidative damage index of liver tissue of rats in each group

| Item | Control group | Low-dose group (0.58 g/kg) | Medium-dose group (1.17 g/kg) | High-dose group (2.92 g/kg) |
|---|---|---|---|---|
| TBARS (µM/g protein) | $0.50 \pm 0.12^b$ | $0.39 \pm 0.07^a$ | $0.39 \pm 0.05^a$ | $0.33 \pm 0.03^a$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

The oxidative damage index of muscle of rats in each group is shown in Table 10. The GPx activity of the low-, medium-, and high-dose groups is significantly higher than that of the control group (p<0.05); the SOD activity of the middle and high-dose groups is higher than that of the control group (p<0.05); the catalase activity of the low-, medium-, and high-dose groups is significantly increased compared with the control group (p<0.05); the GPx, SOD, and catalase activity are not different between each dose group (p>0.05); and each dose group of TBARS is significantly decreased (p<0.05) compared with the control group.

TABLE 10

Analysis results of oxidative damage index of muscle tissue of rats in each group

| Item | Control group | Low-dose group (0.58 g/kg) | Medium-dose group (1.17 g/kg) | High-dose group (2.92 g/kg) |
|---|---|---|---|---|
| GPx (U/g protein) | $26.3 \pm 5.7^a$ | $44.1 \pm 10.9^b$ | $48.4 \pm 7.7^b$ | $44.5 \pm 12.7^b$ |
| SOD (U/mg protein) | $4.2 \pm 1.5^a$ | $5.6 \pm 1.3^{ab}$ | $6.7 \pm 1.1^b$ | $7.0 \pm 1.7^b$ |
| Catalase (U/g protein) | $43.4 \pm 12.7^a$ | $71.8 \pm 12.6^b$ | $80.9 \pm 37.6^b$ | $97.3 \pm 31.4^b$ |
| TBARS (µM/g protein) | $1.90 \pm 0.40^c$ | $1.56 \pm 0.29^b$ | $1.45 \pm 0.20^{ab}$ | $1.22 \pm 0.31^a$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

3.8 Serum Biochemical Analysis

At the end of the event, all test rats were sacrificed for blood sampling by inhaling carbon dioxide. After centrifugation under the conditions of 4° C. and 3,000×g for 15 minutes, serum was obtained and aspartate aminotransferase (AST), alanine aminotransferase (ALT), glucose, blood urea nitrogen (BUN), and creatinine in the serum samples were measured with a serum biochemical analyzer (7070 Autoanalyzer, Hitachi) and related reagents.

The results of serum biochemical tests of the rats in each group are shown in Table 11. There are no significant differences in the values of liver damage indices (AST, ALT) between the groups (p>0.05). There are three types of muscle damage indices (CPK, creatinine, myoglobin), and the values of CPK and creatinine concentrations of the low-, medium-, and high-dose groups are not significantly different from those of the control group (p>0.05). The myoglobin concentration of each dose is significantly increased compared with the control group (p>0.05). There is no significant difference in blood glucose values between the groups (p>0.05).

TABLE 11

Serum biochemical analysis results of rats in each group

| Item | Control group | Low-dose group (0.58 g/kg) | Medium-dose group (1.17 g/kg) | High-dose group (2.92 g/kg) |
|---|---|---|---|---|
| AST (U/L) | $116.8 \pm 17.8^a$ | $116.5 \pm 12.6^a$ | $112.5 \pm 17.0^a$ | $117.5 \pm 26.8^a$ |
| ALT (U/L) | $52.9 \pm 6.5^a$ | $57.0 \pm 10.8^a$ | $60.4 \pm 8.5^a$ | $54.3 \pm 9.1^a$ |
| Creatinine (mg/dL) | $0.45 \pm 0.05^a$ | $0.46 \pm 0.07^a$ | $0.43 \pm 0.05^a$ | $0.45 \pm 0.05^a$ |
| CPK (U/L) | $150.1 \pm 25.4^a$ | $163.3 \pm 37.6^a$ | $165.8 \pm 60.1^a$ | $156.0 \pm 49.6^a$ |
| Myoglobin (U/L) | $2.4 \pm 1.5^a$ | $4.2 \pm 2.0^b$ | $4.5 \pm 1.5^b$ | $4.8 \pm 1.4^b$ |
| Glucose (mg/dL) | $145.1 \pm 20.2^a$ | $140.4 \pm 25.6^a$ | $153.3 \pm 26.3^a$ | $132.8 \pm 30.0^a$ |

All data are expressed as mean±S.D., n=8. The difference between the groups was compared by Duncan's multiple range test of One-Way ANOVA, and the statistical results are represented by English letters. The same letter indicates that there is no statistical difference between the groups (p>0.05), and different letters indicate statistical difference between the groups (p<0.05).

Based on the above, the average bodyweight, average food intake, and liver and kidney weight of rats of each dose group were compared with the control group; the results show that feeding the poultry crude protein extract of the invention had no adverse reaction effects on physiological metabolism. After feeding the low-, medium-, and high doses of the poultry crude protein extract of the invention, the swimming time of the rats compared with the control group is respectively increased from 442.3 seconds to 598.8 seconds, 517.3 seconds, and 585.6 seconds, that is, the increase in swimming time indicates an effect of increased basic physical strength of the rats. In the blood urea nitrogen analysis results, the blood urea nitrogen value of each dose group is significantly lower than the control group, indicating that from the low-dose group, the ability to accelerate protein metabolism is observed, and blood urea nitrogen content is reduced. The change in lactic acid content after the swimming exhaustion test shows that the lactic acid content is increased due to fatigue after the swimming test, and is gradually decreased after rest due to lactic acid metabolism. The results of lactic acid analysis in plasma show that when the rats of each dose group were given the poultry crude protein extract, after the exercise test, the forming of lactic acid was inhibited, and the accumulation of lactic acid was slowed down. The analysis results of muscle glycogen concentration show that each dose group show a significant increase compared with the control group. That is, the muscle glycogen concentration may be increased to improve anti-fatigue effect. The analysis results of serum biochemical indices show that there are no significant differences in the values of liver damage indices (AST, ALT) between the groups; there are no significant differences in the values of muscle damage (CPK, creatinine), indicating that feeding the poultry crude protein extract of the invention had no adverse effects on the safety of the rats. The liver and muscle CPx and catalase activity of each dose group are significantly higher than those of the control group, indicating that after feeding the poultry crude protein extract of the invention, the activity of antioxidant enzymes was enhanced to form a protective effect. In terms of oxidative damage index, TBARS is one of the lipid peroxidation lipid indices. Therefore, after vigorous exercise, the lipid peroxide is increased significantly. The results show that the poultry crude protein extract of the invention may significantly reduce the TBARS values of the liver and muscle, and the dose groups showed significant difference in the alleviation of the lipid peroxidation phenomenon of the liver and muscle. Therefore, the poultry crude protein extract of the invention has the effects of increasing muscle glycogen concentration, helping to increase exercise tolerance, helping to increase blood urea nitrogen metabolism, and helping to inhibit lactic acid production.

What is claimed is:

1. A method for improving fatigue tolerance of a user, comprising:
   feeding a poultry crude protein for improving fatigue factors of the user,
   wherein a total molar ratio of amino acids of the poultry crude protein extract is 100, the poultry crude protein extract comprises the following amino acids in molar ratio: 17.5-20.5% leucine, 8.0-9.5% isoleucine, 13.0-14.5% valine, 6.5-8.5% histidine, 12.0-13.5% threonine, 20.5-22.5% lysine, 8.0-11.5% phenylalanine, 1.5-3.0% tyrosine and 4.5-5.5% methionine.

2. The method of claim 1, wherein an effective dose of the poultry crude protein extract is at least 20 mL per day.

3. The method of claim 1, wherein the improving fatigue tolerance of the user comprises:
   increasing a muscle glycogen concentration.

4. The method of claim 1, wherein the improving fatigue tolerance of the user comprises:
   increasing an exercise tolerance.

5. The method of claim 1, wherein the improving fatigue tolerance of the user comprises:
   increasing a blood urea nitrogen metabolism.

6. The method of claim 1, wherein the improving fatigue tolerance of the user comprises:
   inhibiting a lactic acid production.

7. The method of claim 1, wherein the poultry crude protein extract is obtained by an extraction of a poultry meat at a high temperature of 85° C. to 105° C. and a high pressure for 9 hours to 11 hours with a subsequent removal of a fat by an oil and water separation.

8. The method of claim 7, wherein a source of the poultry meat is chicken, duck, goose, or pigeon.

9. The method of claim 1, wherein the improving fatigue tolerance of the user comprises:
   accelerating a protein metabolism ability.

10. The method of claim 1, wherein the improving fatigue tolerance of the user comprises:
    decreasing a lactate increase rate.

11. The method of claim 1, wherein the improving fatigue tolerance of the user comprises:
    increasing an antioxidant enzymes activity.

* * * * *